(12) United States Patent
Kato et al.

(10) Patent No.: US 8,785,675 B2
(45) Date of Patent: Jul. 22, 2014

(54) MIXED CATALYST

(75) Inventors: Takaaki Kato, Tokyo (JP); Minoru Kadowaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/697,053

(22) PCT Filed: Mar. 23, 2011

(86) PCT No.: PCT/JP2011/056941
§ 371 (c)(1),
(2), (4) Date: Nov. 9, 2012

(87) PCT Pub. No.: WO2011/142178
PCT Pub. Date: Nov. 17, 2011

(65) Prior Publication Data
US 2013/0053596 A1  Feb. 28, 2013

(30) Foreign Application Priority Data

May 13, 2010  (JP) .................. 2010-111422
May 13, 2010  (JP) .................. 2010-111444

(51) Int. Cl.
*C07C 255/06* (2006.01)
*C07C 255/07* (2006.01)

(52) U.S. Cl.
USPC ...................................... 558/303

(58) Field of Classification Search
USPC ........................................ 558/303
See application file for complete search history.

(56) References Cited

U.S. PATENT DOCUMENTS

| 6,429,332 B1 | 8/2002 | Tanimoto et al. |
| 6,518,216 B1 | 2/2003 | Han et al. |
| 2003/0088118 A1 | 5/2003 | Komada et al. |
| 2004/0192966 A1 | 9/2004 | Hazin et al. |
| 2008/0064590 A1 | 3/2008 | Bogan et al. |
| 2010/0240921 A1* | 9/2010 | Tateno et al. ............. 558/308 |

FOREIGN PATENT DOCUMENTS

| JP | 8-47641 A | 2/1996 |
| JP | 10-28862 A | 2/1998 |
| JP | 2001-79412 A | 3/2001 |
| JP | 2006-77557 A | 3/2006 |
| JP | 2007-530257 A | 11/2007 |
| JP | 2008-62231 A | 3/2008 |
| KR | 2003-0003238 A | 1/2003 |
| WO | WO 2007/119376 A1 | 10/2007 |
| WO | WO 2009/048553 A2 | 4/2009 |
| WO | WO-2009048553 * | 4/2009 |

OTHER PUBLICATIONS

International Search Report issued in PCT/JP2011/056941, mailed on Jul. 5, 2011.

* cited by examiner

*Primary Examiner* — Yong Chu
*Assistant Examiner* — Sonya Wright
(74) *Attorney, Agent, or Firm* — Birch, Stewart, Kolasch & Birch, LLP

(57) ABSTRACT

It is an object of the present invention to provide a mixed catalyst for a vapor-phase catalytic oxidation or a vapor-phase catalytic ammoxidation reaction of propane, or isobutene, capable of providing a corresponding unsaturated acid or unsaturated nitrile at high yield from propane or isobutene.

5 Claims, No Drawings

MIXED CATALYST

BACKGROUND OF THE INVENTION

1. Field of the Invention

The present invention relates to a mixed catalyst and a method for producing an unsaturated acid or an unsaturated nitrile using the mixed catalyst.

2. Description of the Related Art

Conventionally, a method for subjecting propylene or isobutylene to a vapor-phase catalytic oxidation reaction or a vapor-phase catalytic ammoxidation reaction to produce a corresponding unsaturated carboxylic acid or unsaturated nitrile has been well known. In recent years, attention has been directed to a method for subjecting propane or isobutane in place of propylene or isobutylene to a vapor-phase catalytic oxidation or a vapor-phase catalytic ammoxidation to produce a corresponding unsaturated carboxylic acid or unsaturated nitrile.

Hitherto, various oxide catalysts have been proposed as a catalyst used for the vapor-phase catalytic ammoxidation. Although an oxide obtained by mixing and calcining molybdenum and vanadium or the like as necessary is generally used as a catalyst as it is, a technique for further subjecting the calcined catalyst to a post-treatment in producing an unsaturated carboxylic acid or an unsaturated nitrile has also been studied.

For example, Japanese Patent Laid-Open No. 10-028862 discloses a technique for impregnating a Mo—V—Sb/Te-based catalyst with a solution containing one or more elements selected from the group consisting of tungsten, molybdenum, chromium, zirconium, titanium, niobium, tantalum, vanadium, boron, bismuth, tellurium, palladium, cobalt, nickel, iron, phosphor, silicon, rare-earth elements, alkali metals, and alkali earth metals.

Japanese Patent Laid-Open No. 2008-062231 discloses a technique for bringing a mixed metal oxide catalyst into contact with water, and optionally an aqueous metal oxide precursor to produce a modified mixed metal oxide, and calcining the obtained modified mixed metal oxide.

Japanese Patent Laid-Open No. 2006-077557 discloses a technique for immersing tungsten and manganese in a Mo—V—Sb—Nb-based catalyst.

International Publication WO 2009-048553 discloses a technique for mixing a catalyst with a modifier such as an antimony compound, a molybdenum compound, a tellurium compound, and a tungsten compound, and subjecting the obtained catalyst to a reaction, or mixing a catalyst or a catalyst precursor with a modifier, calcining the obtained mixture, and subjecting the calcined product to a reaction.

However, when the present inventors used the oxide catalysts disclosed in Japanese Patent Laid-Open No. 10-028862, Japanese Patent Laid-Open No. 2008-062231, and Japanese Patent Laid-Open No. 2006-077557 for the vapor-phase catalytic oxidation or the vapor-phase catalytic ammoxidation reaction of propane or isobutane, all the catalysts provided an insufficient yield of the target product.

The producing methods described in Japanese Patent Laid-Open No. 10-028862, Japanese Patent Laid-Open No. 2008-062231, Japanese Patent Laid-Open No. 2006-077557, and International Publication WO 2009-048553 describe improvement in performance of the Mo—V—Te/Sb-based composite oxide having activity as it is by impregnating the composite oxide with tungsten or immersing tungsten in the composite oxide. However, the composite oxide before the impregnation or the immersion does not contain tungsten, and a catalyst providing a high yield of the target product has not yet been obtained.

In view of the above-mentioned situation, it is an object of the present invention to provide a mixed catalyst for a vapor-phase catalytic oxidation or a vapor-phase catalytic ammoxidation reaction of propane or isobutane, capable of providing a corresponding unsaturated acid or unsaturated nitrile at high yield from propane or isobutane. It is another object of the present invention to provide a method for producing an unsaturated acid or an unsaturated nitrile using the mixed catalyst.

SUMMARY OF THE INVENTION

The present inventors have conducted intensive research in order to solve the above-mentioned problems. As a result, the present inventors discovered that when a Mo—V—Nb—W-based composite oxide and a tungsten compound are mixed, functions of tungsten contained in the composite oxide before the mixture and the tungsten compound in the mixed catalyst are different from each other. As a result, the present inventors found that the mixed catalyst containing the Mo—V—Nb—W-based composite oxide and the tungsten compound at a specific ratio can solve the problems. The present invention was accomplished on the basis of this finding.

That is, the present invention is as follows:

[1]
A mixed catalyst for a vapor-phase catalytic oxidation reaction or a vapor-phase catalytic ammoxidation reaction of propane or isobutane,
the mixed catalyst comprising:
(a) a composite oxide represented by the following composition formula (1):

$$Mo_1V_aNb_bSb_cW_dZ_eO_n \tag{1}$$

wherein Z represents at least one element selected from the group consisting of La, Ce, Pr, Yb, Y, Sc, Sr, and Ba; each of a, b, c, d, e, and n represents an atomic ratio of each element based on Mo atom; a is in a range of $0.01 \leq a \leq 1$; b is in a range of $0.01 \leq b \leq 1$; c is in a range of $0.01 \leq c \leq 1$; d is in a range of $0.01 \leq d \leq 1$; e is in a range of $0 \leq e \leq 1$; and n represents a number determined by a valence of a component metal; and
(b) a tungsten compound at a ratio of the following formula (2):

$$0.001 < w < 0.3 \tag{2}$$

wherein w represents an atomic ratio of tungsten in the tungsten compound as an atomic ratio based on Mo atom in the composite oxide.

[2]
The mixed catalyst according to the above-mentioned item [1], wherein the tungsten compound contains tungsten oxide.

[3]
The mixed catalyst according to the above-mentioned item [1] or [2], wherein the mixed catalyst is used for a fluidized bed reaction.

[4]
A method for producing an unsaturated acid or an unsaturated nitrile, including a step of contacting propane or isobutane and oxygen with the mixed catalyst of any of the above-mentioned items [1] to [3], or contacting propane or isobutane, and oxygen and ammonia with the mixed catalyst of any of the above-mentioned items [1] to [3].

[5]
The method according to the above-mentioned item [4], wherein a temperature for the step of contacting is set to 400° C. or more.

A corresponding unsaturated acid or unsaturated nitrile can be produced at high yield from propane or isobutane by using a mixed catalyst of the present invention.

DETAILED DESCRIPTION OF THE PREFERRED EMBODIMENT

Hereinafter, an embodiment of the present invention (hereinafter, referred to as "the present embodiment") will be described in detail. The present invention is not limited to the following embodiment, and many variations may be made within the scope of the present invention.

A mixed catalyst of the present embodiment is a mixed catalyst for a vapor-phase catalytic oxidation reaction or a vapor-phase catalytic ammoxidation reaction of propane or isobutane.

The mixed catalyst comprises:

(a) a composite oxide represented by the following composition formula (1):

$$Mo_1V_aNB_bSb_cW_dZ_eO_n \quad (1)$$

wherein Z represents at least one element selected from the group consisting of La, Ce, Pr, Yb, Y, Sc, Sr, and Ba; each of a, b, c, d, e, and n represents an atomic ratio of each element based on Mo atom; a is in a range of $0.01 \leq a \leq 1$; b is in a range of $0.01 \leq b \leq 1$; c is in a range of $0.01 \leq c \leq 1$; d is in a range of $0.001 \leq d \leq 1$; e is in a range of $0 \leq e \leq 1$; and n represents a number determined by a valence of a component metal; and (b) a tungsten compound at a ratio of the following formula (2):

$$0.001 < w < 0.3 \quad (2)$$

wherein w represents an atomic ratio of tungsten in the tungsten compound as an atomic ratio based on Mo atom in the composite oxide.

Although a method for producing the mixed catalyst of the present embodiment is not particularly limited, an example thereof will be described below.

[1] Method for Producing Mixed Catalyst

The composite oxide contained in the mixed catalyst of the present embodiment can be produced, for example, by the following method.

(a) Production of Composite Oxide

The composite oxide is produced via the following three steps.

(1) a step of preparing raw materials to obtain a raw material-prepared solution;

(2) a step of drying the raw material-prepared solution obtained in the step (1) to obtain dry powder;

(3) a step of calcining the dry powder obtained in the step (2) to obtain a composite oxide.

The term "preparing" in the above-mentioned step (1) means to dissolve or disperse raw materials of the composite oxide in an aqueous solvent. The term "raw material" means a compound containing an element composing the composite oxide.

The raw material is not particularly limited, and, for example, such compounds as described below can be used.

As for raw materials for Mo and V, ammonium heptamolybdate: $[(NH_4)_6Mo_7O_{24} \cdot 4H_2O]$ and ammonium metavanadate: $[NH_4VO_3]$ can appropriately be used, respectively, although the raw materials are not particularly limited.

As raw materials for Nb, niobic acid, an inorganic niobate and an organic niobate can appropriately be used. Of these, niobic acid is particularly preferable. Niobic acid is a compound represented by $Nb_2O_5 \cdot nH_2O$ and is also referred to as niobium hydroxide or niobium oxide hydrate. Further, a Nb raw material solution in which a molar ratio of dicarboxylic acid/niobium is 1 to 4 is also preferably used as the raw materials for Nb. As the dicarboxylic acid, oxalic acid is preferable.

As raw materials for Sb, diantimony trioxide $[Sb_2O_3]$ is preferable, although not particularly limited.

Raw materials for W are not particularly limited. A compound containing W and a solution in which metal of W is solubilized in an appropriate solvent can be used. Examples of the compound containing W include an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of W. Of these, an aqueous raw material such as a nitrate, and a carboxylate of W is appropriately used.

Raw materials for a component Z are not particularly limited as long as the raw materials contain at least one element selected from the group consisting of La, Ce, Pr, Yb, Y, Sc, Sr, and Ba. A compound containing the above-mentioned element and a solution in which the metal of the above-mentioned element is solubilized in an appropriate solvent can be used. Examples of the compound containing the element include a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of the metal element. Of these, an aqueous raw material such as a nitrate, and a carboxylate is appropriately used.

When the composite oxide is a silica carrier, silica sol can be used as a raw material for silica. However, silica powder can be used either partially or entirely as the silica raw material. The silica powder is preferably produced by a high-temperature method. The silica powder is used with the silica powder previously dispersed in water to facilitate the addition and mixture of the silica powder to a slurry. A dispersing method is not particularly limited. The silica powder can be dispersed by using a general homogenizer, homomixer, and supersonic vibrator or the like either singly or in combination.

Hereinafter, appropriate production examples of the composite oxide including steps (1) to (3) will be described.

(Step (1): Step of Preparing Raw Materials)

In step (1), a Mo compound, a V compound, an Sb compound, a W compound, a component Z compound, and optionally, a component which becomes any other raw materials are added to water and, then, heated, thereby preparing an aqueous mixed-solution (I). On this occasion, an inside of a container preparing the mixed-solution (I) may be in a nitrogen atmosphere. A Nb compound and a dicarboxylic acid are then heated in water while stirring, thereby preparing a mixed-solution ($B_0$). Further, hydrogen peroxide is added to the mixed-solution ($B_0$), thereby preparing an aqueous mixed-solution (II). On this occasion, $H_2O_2/Nb$ (molar ratio) is preferably 0.5 to 20, and more preferably 1 to 10.

Next, depending on a composition to be targeted, the aqueous mixed-solution (I) and the aqueous mixed-solution (II) are appropriately mixed, thereby obtaining an aqueous mixed-solution (III). The obtained aqueous mixed-solution (III) is aged under an air atmosphere, thereby obtaining a slurry raw material-prepared solution (hereinafter, also simply referred to as "a slurry").

Herein, aging of the aqueous mixed-solution (III) means to leave standstill or stir the aqueous mixed-solution (III) for a predetermined time. When the composite oxide is industrially produced, a spray dryer usually has a rate-limiting treatment speed. After a portion of the aqueous mixed-solution (III) is spray-dried, it takes time to complete the spray drying of the whole mixed-solution. In the meantime, the aging of the mixed-solution which is not spray-dried is continued. Therefore, an aging time includes not only an aging time before spray drying but also a time from the start to finish of the spray drying.

The aging time is preferably 90 minutes or more and within 50 hours, and more preferably 90 minutes or more and within 6 hours from the viewpoint of yield of a target product.

An aging temperature is preferably 25° C. or more from the viewpoint of preventing the condensation of a Mo component and the deposition of V. The aging temperature is preferably 65° C. or less from the viewpoint of preventing the excessive generation of the hydrolysis of a complex containing Nb and hydrogen peroxide and forming a slurry in a preferable form. Therefore, the aging temperature is preferably 25° C. or more and 65° C. or less, and more preferably 30° C. or more and 60° C. or less.

An atmosphere in the container in aging preferably has a sufficient oxygen concentration. Insufficient oxygen may hardly cause substantial change of the aqueous mixed-solution (III). An oxygen concentration (hereinafter, also referred to as "a vapor-phase oxygen concentration") of a vapor-phase part in the container is preferably 1 vol % or more.

The vapor-phase oxygen concentration in the container can be measured by general methods. For example, the vapor-phase oxygen concentration can be measured using a zirconia type oxygen meter. A place where the vapor-phase oxygen concentration is measured is preferably near an interface between the aqueous mixed-solution (III) and vapor phase. For example, preferably, the vapor-phase oxygen concentration is measured three times at the same point within 1 minute, and the mean value of the three measurement results is used as the vapor-phase oxygen concentration.

A dilution gas for reducing the vapor-phase oxygen concentration is not particularly limited. Examples of the dilution gas include nitrogen, helium, argon, carbon dioxide, and steam. Industrially, nitrogen is preferable. As a gas for increasing the vapor-phase oxygen concentration, pure oxygen or air with a high oxygen concentration is preferable.

Some change is considered to occur in an oxidation/reduction state of the component contained in the aqueous mixed-solution (III) by the above-mentioned aging. The occurrence of some change is suggested from the occurrence of change in color and change in an oxidation-reduction potential, or the like of the aqueous mixed-solution (III) during the aging. As a result, the difference between the composite oxides occurs, which are obtained by the presence or absence of the aging for 90 minutes or more and within 50 hours in an atmosphere having an oxygen concentration of 1 to 25 vol %. For example, it is extremely difficult to correctly identify change in the form of the component in the liquid during the aging. However, composite oxides having a different aging time are produced, and yield of a target product is evaluated using the composite oxides as a catalyst, thereby finding that an aging time imparted to a catalyst having a good yield is preferable. On this occasion, a slurry having some preferable form can be estimated to be formed.

It is considered that the oxidation-reduction potential of the aqueous mixed-solution (III) is controlled by a potential (600 mV/AgCl) of an aqueous raw-material solution (II), and that Nb oxalate peroxide contained and other metal components in the aqueous raw-material solution (II) cause some oxidation-reduction reaction to cause temporal reduction in the potential. The oxidation-reduction potential of the aqueous mixed-solution (III) is preferably 450 to 530 mV/AgCl, and more preferably 470 to 510 mV/AgCl.

The oxygen concentration during the aging is preferably 1 vol % or more from the viewpoint of preventing excessive delay in the progress of the oxidation-reduction reaction having an influence on change in the oxidation/reduction state of the components contained in the aqueous mixed-solution (III), and preventing some excessive oxidation of the oxidation/reduction state in the slurry. On the other hand, the oxygen concentration during the aging is preferably 25 vol % or less from the viewpoint of preventing some excessive reduction of the slurry caused by the excessive progress of the oxidation-reduction reaction. Anyhow, it is necessary to maintain the oxygen concentration in an appropriate range since vapor-phase oxygen has an influence on the oxidation-reduction condition of the slurry. The range is more preferably 5 to 23 vol %, and still more preferably 10 to 20 vol %.

When the composite oxide is a silica carrier, a raw material-prepared solution containing silica sol is prepared. The silica sol can appropriately be added thereto. An aqueous dispersion of the silica powder can be used as a portion of the silica sol. The aqueous dispersion of the silica powder can also appropriately be added.

Hydrogen peroxide is preferably added to the aqueous mixed-solution (I) or a liquid containing components of the aqueous mixed-solution (I) during preparation. On this occasion, $H_2O_2/Sb$ (molar ratio) is preferably 0.01 to 5, and more preferably 0.05 to 4. On this occasion, stirring is preferably continued at 30° C. to 70° C. for 30 minutes to 2 hours.

(Step (2): Drying Step)

In a step (2), a slurry obtained in a raw material preparing step is dried, thereby obtaining dry powder. Drying can be performed by known methods such as spray drying or evaporation to dryness. Of these, minute spherical dry powder is preferably obtained by the spray drying. Spraying in the spray drying method can be performed by a centrifugal system, a two-fluid-nozzle system, or a high-pressure nozzle system. Air heated by steam, and an electric heater or the like can be used as a heat source for drying. An inlet temperature of a dryer of a spray drying device is preferably 150 to 300° C. An outlet temperature of the dryer is preferably 100 to 160° C.

(Step (3): Calcining Step)

In a step (3), a composite oxide is obtained by calcining the dry powder obtained in the drying step. For example, a rotary kiln can be used as a calcining apparatus. The shape of a calcining device is not particularly limited. However, the shape of the calcining device is preferably tubular since continuous calcination can be carried out. The shape of a calcining tube is not particularly limited. However, the shape of the calcining tube is preferably cylindrical.

A heating system is preferably an external heating system. For example, an electric furnace can appropriately be used. The size and material or the like of the calcining tube can be suitably selected depending on a calcining condition and a production amount. The inner diameter of the calcining tube is preferably 70 to 2000 mm, and more preferably 100 to 1200 mm. The length of the calcining tube is preferably 200 to 10000 mm, and more preferably 800 to 8000 mm. When an impact is imparted to the calcining device, the thickness of the calcining device is preferably 2 mm or more, and more preferably 4 mm or more from the viewpoint that the calcining device has an enough thickness not to be broken by the impact. The thickness of the calcining device is preferably 100 mm or less, and more preferably 50 mm or less from the viewpoint that the impact is sufficiently transmitted into the calcining tube. The material of the calcining tube is not particularly limited as long as the calcining tube has heat resistance and strength not to be broken by the impact. SUS can be appropriately used as the material of the calcining tube.

A weir plate having a central part having a hole through which powder passes is provided vertically to the flow of the powder in the calcining tube, and thereby the calcining tube can be also partitioned into two or more zones. A holding time in the calcining tube is easily secured by disposing the weir plate. The number of the weir plates may be one or more. The material of the weir plate is preferably a metal, and a weir plate made of the same material as that of the calcining tube can appropriately be used. The height of the weir plate can be adjusted in accordance with a holding time which should be secured. For example, when powder is supplied at 250 g/hr using a rotary kiln having a calcining tube having an inner diameter of 150 mm and a length of 1150 mm and made of SUS, the height of the weir plate is preferably 5 to 50 mm, more preferably 10 to 40 mm, and still more preferably 13 to 35 mm. The thickness of the weir plate is not particularly limited, and is preferably adjusted in accordance with the size of the calcining tube. For example, in the case of a rotary kiln having a calcining tube having an inner diameter of 150 mm and a length of 1150 mm and made of SUS, the thickness of the weir plate is preferably 0.3 mm or more and 30 mm or less, and more preferably 0.5 mm or more and 15 mm or less.

In order to prevent crack and crazing or the like of the dry powder and to uniformly calcine the dry powder, the calcining tube is preferably rotated during calcining. The rotation speed of the calcining tube is preferably 0.1 to 30 rpm, more preferably 0.5 to 20 rpm, and still more preferably 1 to 10 rpm.

As the calcination of the dry powder, preferably, the heating temperature of the dry powder is continuously or intermittently raised to a temperature in the range of 550 to 800° C. from a temperature lower than 400° C.

A calcining atmosphere may be under an air atmosphere or under an air flow. However, at least a portion of the calcination is preferably carried out while an inert gas which does not substantially contain oxygen, such as nitrogen, flows. The supplied amount of the inert gas is preferably 50 N liters or more based on 1 kg of the dry powder, more preferably 50 to 5000 N liters, and still more preferably 50 to 3000 N liters (N liter means a liter measured under normal temperature and pressure conditions, that is, at 20° C. and 1 atm). On this occasion, the flows of inert gas and dry powder may be in the form of a counter flow or a parallel flow. However, counter flow contact is preferable in consideration of gas components generated from the dry powder and a trace amount of air entering together with the dry powder.

The calcining step can be carried out in a single stage. However, the calcination preferably includes pre-stage calcination performed in the temperature range of 250 to 400° C. and main calcination performed in the temperature range of 550 to 800° C. The pre-stage calcination and the main calcination may be continuously carried out. The main calcination may be carried out anew once the pre-stage calcination has been completed. The pre-stage calcination and the main calcination may each be divided into several stages.

The pre-stage calcination is performed, preferably under an inert gas flow at a heating temperature of 250° C. to 400° C., and preferably 300° C. to 400° C. The pre-stage calcination is preferably held at a constant temperature within the temperature range of 250° C. to 400° C. However, a temperature may fluctuate within the temperature range of 250° C. to 400° C., or be gradually raised or lowered. The holding time of the heating temperature is preferably 30 minutes or more, and more preferably 3 to 12 hours.

A temperature raising pattern until the pre-stage calcining temperature is reached may be linearly raised, or a temperature may be raised so that an arc of an upward or downward convex is formed.

A mean temperature raising rate during temperature raising until the pre-stage calcining temperature is reached is not particularly limited. However, the mean temperature raising rate is generally about 0.1 to 15° C./min, preferably 0.5 to 5° C./min, and more preferably 1 to 2° C./rain.

The main calcination can be carried out, preferably under an inert gas flow, preferably at 550 to 800° C., more preferably at 580 to 750° C., still more preferably at 600 to 720° C., and particularly preferably at 620 to 700° C. The main calcination is preferably held at a constant temperature within the temperature range of 620° C. to 700° C. However, a temperature may fluctuate within the temperature range of 620° C. to 700° C., or be gradually raised or lowered. The time of the main calcination is preferably 0.5 to 20 hours, and more preferably 1 to 15 hours.

When the calcining tube is partitioned with a weir plate, the dry powder and/or a composite oxide continuously passes through at least 2 zones, preferably 2 to 20 zones, and more preferably 4 to 15 zones. A temperature can be controlled using one or more controllers. However, in order to obtain the desired calcining temperature pattern, a heater and a controller are preferably disposed in each of the zones partitioned with these weir plates to control the temperature. For example, when the seven weir plates are disposed so that a length of portion of the calcining tube entering a heating furnace is equally divided into eight, and the calcining tube partitioned into the eight zones is used, the setting temperature of each of the eight zones is preferably controlled by the heater and the controller disposed in each of the zones so that the temperature of the dry powder and/or the composite oxide has the desired calcining temperature pattern. An oxidizing component (for example, oxygen) or a reducing component (for example, ammonia) may be added to the calcining atmosphere under the inert gas flow as necessary.

A temperature raising pattern until the main calcining temperature is reached may be linearly raised, or a temperature may be raised so that an arc of an upward or downward convex is formed.

A mean temperature raising rate in temperature raising until the main calcining temperature is reached is not particularly limited. However, the mean temperature raising rate is generally about 0.1 to 15° C./min, preferably 0.5 to 10° C./min, and more preferably 1 to 8° C./min.

A mean temperature lowering rate after the main calcination is completed is 0.01 to 1000° C./min, preferably 0.05 to 100° C./min, more preferably 0.1 to 50° C./min, and particularly preferably 0.5 to 10° C./min. After the main calcination is completed, a temperature lower than the main calcining temperature is also preferably held once. A holding temperature is lower than the main calcining temperature by 10° C. or more, preferably 50° C. or more, and more preferably 100° C. or more. A holding time is 0.5 hours or more, preferably 1 hour or more, more preferably 3 hours or more, and particularly preferably 10 hours or more.

When the main calcination is carried out anew once the pre-stage calcination has been completed, a low temperature treatment is preferably performed in the main calcination.

A time required for the low temperature treatment, that is, a time required for reducing the temperature of the dry powder and/or the composite oxide and raising the temperature to the calcining temperature can appropriately be adjusted by the size, the thickness, and the material of the calcining device, a catalyst production amount, a series of periods for continuously calcining the dry powder and/or the composite oxide, and a fixing rate and a fixing amount, or the like. For example, when a calcining tube having an inner diameter of 500 mm, a length of 4500 mm, and a thickness of 20 mm, and made of SUS is used, the time required for the low temperature treatment is preferably within 30 days during the series of periods for continuously calcining a catalyst, more preferably within 15 days, still more preferably within 3 days, and particularly preferably within 2 days.

For example, when dry powder is supplied at a rate of 35 kg/hr while a rotary kiln having a calcining tube having an inner diameter of 500 mm, a length of 4500 mm, and a thickness of 20 mm and made of SUS is rotated at 6 rpm, and main calcination is performed at a main calcining temperature of 645° C., a step of lowering a temperature to 400° C. and raising the temperature to 645° C. can be performed in about 1 day. When calcination is continuously performed for 1 year, the calcination can be performed by carrying out such low temperature treatment once a month while a temperature of an oxide layer is stably maintained.

In the calcining step, a portion of a compound having a low melting point in an oxide crystal may be crystallized in a protruded state on a surface of a composite oxide particle. Since the crystal of the low melting point compound is exuded in a protruded state on the surface of the catalyst, the crystal may block fluidity when the catalyst is used in a fluid bed reaction. Therefore, in the case of the catalyst for the fluid bed reaction, preferably, the crystal of the low melting point compound derived in a protruded state is physically removed prior to using the catalyst from the viewpoint of preventing the reduction of the fluidity. When the crystal of the low melting point compound is removed from the surface of the catalyst, the crystal may be removed before a mixing step of a tungsten source to be described below, or may be removed after the mixing step.

(b) Mixing Step of Tungsten Source

The composite oxide of the present embodiment has catalyst activity as it is. When a mixed catalyst contains a tungsten compound and a composite oxide at a specific ratio, yield of a target product is enhanced.

As a method for obtaining the mixed catalyst containing the tungsten compound, an example of a step of mixing a supply source of the tungsten compound (hereinafter, also referred to as "a tungsten source") and the composite oxide will be described.

(b-1) Tungsten Source

Examples of the tungsten source include an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, an alkoxide, a triphenyl compound, a polyoxometalate, and an ammonium salt of a polyoxometalate of tungsten; a powder raw material such as tungsten oxide, tungstate, ammonium para tungstate, tungstosilicic acid, silicotungstomolybdic acid, and vanadotungstosilicic acid; and a liquid raw material such as an aqueous solution of ammonium metatungstate and tungsten oxide sol.

The type of the tungsten source and the mixture of the tungsten source in a solid form or a liquid form can be selected depending on any mixing step, or the composition of the mixed catalyst to be prepared, or the like. As described below, the mixing step includes a method for intactly supplying the tungsten source in a solid state, and a method for supplying the tungsten source in a liquid state. In the case of the method for supplying the tungsten source in a liquid state, a commercially available liquid raw material such as the aqueous solution of ammonium metatungstate may be used. However, needless to say, the above-mentioned powder raw material may be used with the powder raw material dissolved and/or dispersed in a solvent. In this case, an appropriate amount of the powder raw material may be dissolved and/or dispersed in water, acetone, methanol, ethanol, and other polar/nonpolar solvent. Water is preferably used as a solvent and/or a dispersion medium in view of handling easiness, depending on solubility or the like. When powder is directly mixed without using the solvent, tungsten oxide is preferable from the viewpoint of the influence of the tungsten compound on the target product, more preferably tungsten oxide having a tungsten bronze structure, and still more preferably tungsten trioxide.

The mixed catalyst of the present embodiment can be obtained by physically or chemically mixing the composite oxide and the tungsten source at a predetermined ratio.

(b-2) Physical Mixing Method

A physical mixing method of the composite oxide and the tungsten source is not particularly limited. Examples of the physical mixing method include a method for adding a composite oxide into a hopper supplying a catalyst to a reactor, and adding an appropriate amount of a tungsten source thereto. The composite oxide and the tungsten source may be previously mixed before the composite oxide and the tungsten source are put into the hopper. However, even if the composite oxide and the tungsten source are not previously mixed, the composite oxide and the tungsten source are naturally mixed in the step of supplying the catalyst to the reactor from the hopper, and thereby the previous mixture is not indispensable. The order for putting the composite oxide and the tungsten source into the hopper is not particularly limited either. The order may be appropriately determined so that the composite oxide and the tungsten source are sufficiently bought into contact with each other in the reactor from the viewpoint of the particle diameters or the like of both the composite oxide and the tungsten source. The composite oxide and the tungsten source can also be mixed with air and nitrogen flowing, if needed. In the case of a fluidized bed reaction, the composite oxide and the tungsten source are not supplied at once from the hopper, but the composite oxide and the tungsten source may be supplied in order into the reactor. In this case, the composite oxide and the tungsten source are mixed while the composite oxide and the tungsten source flow in the reactor during the reaction progress.

Since chemical change does not occur in the tungsten source before the production reaction of an unsaturated acid or an unsaturated nitrile in the case of the physical mixing method, the tungsten compound contained in the mixed catalyst has the same structure as that of the tungsten source. On the other hand, when the production reaction of the unsaturated acid or the unsaturated nitrile is progressed using this mixed catalyst, heat or the like is applied to the tungsten compound with the tungsten compound brought into contact with the composite oxide and a reactive substrate, and thereby the chemical change occurs. The mixed catalyst of the present embodiment intends to act on the composite oxide in accordance with the structural change during the reaction progress to bring the influence on catalyst performance. Therefore, when a mixed catalyst is present as a mixture before the reaction even if the structure of a portion or the whole of the tungsten compound is changed to, for example, that of a portion of the composite oxide during the reaction progress, the mixed catalyst is naturally in the category of the mixed catalyst of the present embodiment.

Even if the tungsten source is supplied to a fluidized bed reactor during the reaction progress, the same effect as for that supplied before the reaction occurs. In this case, it is said that the mixed catalyst is produced immediately after the supply of the tungsten source although the mixed catalyst is not present before the reaction.

(b-3) Chemical Mixing Method
(b-3-i) Liquid Phase Step

In the present embodiment, a method for dropping a solution containing a tungsten source dissolved therein into a composite oxide is referred to as impregnation. On the other hand, a method for adding a composite oxide to a solution containing a tungsten source dissolved therein, and bringing the composite oxide into contact with the solution for a certain time by stirring or the like is referred to as immersion. In each case, an unnecessary solution can be removed by filtering or evaporating. The evaporation is carried out at about 30 to 300° C., and preferably 40 to 250° C. A calcining treatment can be then performed if needed, and thereby a portion or the whole amount of the tungsten source can also be converted into an oxide. Fine pores of the composite oxide are filled with an atmosphere gas present before the contact treatment of the composite oxide, such as air and inert gas. The atmosphere gas may block the diffusion of tungsten into the fine pores. In this case, the gas in the fine pores can also be removed in a pressure-reduced atmosphere before the impregnation and the immersion, or during the impregnation and the immersion.

When the impregnation and the immersion are performed, the ion exchange of a metal element and tungsten in the composite oxide may be carried out while the composite oxide and the tungsten source are present in a liquid phase. When the ion exchange occurs, surface modification caused by the ion exchange is expected to progress during a treatment in the liquid phase. However, tungsten is taken into the composite oxide. In this case, tungsten is not present as a simple substance of the tungsten compound in the mixed catalyst, but is a portion of the composite oxide, and it can be hardly said that the catalyst is a mixture. Thereby, the catalyst is not included in the mixed catalyst of the present embodiment. The catalyst in which tungsten is taken into the composite oxide, and the mixed catalyst are compared in respect of the performance of the catalyst. When the catalyst in which tungsten is taken into the composite oxide is used for a production reaction of an unsaturated acid or an unsaturated nitrile, yield of a target product represents a maximum value at the reaction initial stage. The yield may be then reduced, but the yield is not enhanced. On the other hand, in the case of the mixed catalyst, yield of a target product tends to be enhanced with the lapse of time until a certain reaction time, as described below.

The ion exchange in the liquid phase depends on pH, a liquid temperature, a concentration of tungsten in a solution, and a contact time of the solution and the composite oxide, or the like. However, for example, the ion exchange can be suppressed by adjusting pH to 1.0 to 7.0, and preferably 1.0 to 4.0. Preferably, the liquid temperature is generally low. The ion exchange can be suppressed by adjusting the liquid temperature to, for example, 0 to 50° C., and more preferably 0 to 30° C. When the concentration of tungsten is low, the ion exchange can hardly progress. A preferable concentration thereof is less than 1.0 mol/kg as a tungsten metal concentration. The contact time of the solution and the composite oxide is preferably short. The contact time is within 1 hour, and more preferably within 15 minutes.

Although the mixture obtained by the impregnation step and/or the immersion step can be used as the mixed catalyst as it is, the mixture may be used after calcining.

The tungsten compound contained in the mixed catalyst after the liquid phase treatment may also have an aspect in which the tungsten source is changed (for example, oxidization, crystallization, noncrystallization) in addition to an aspect in which the tungsten compound has the same structure as that of the tungsten source. However, the mixed catalyst of each aspect is in the category of the mixed catalyst of the present embodiment as long as the mixed catalyst of the aspect contains the tungsten compound which is not a portion of the composite oxide.

(b-3-ii) Calcining Step

When ion exchange does not occur in a liquid phase, an exchange reaction may occur in a calcining step to convert a tungsten source into a portion of a composite oxide. Surface modification is expected to progress in the exchange reaction to bring about a state where a mixed catalyst is not a mixture, as well as the liquid phase treatment. Easiness of the occurrence of the exchange reaction mainly depends on a calcining temperature. When the calcining temperature is excessively high, the exchange reaction tends to progress. A calcining temperature at which the exchange reaction hardly occurs is preferably 200 to 400° C., and more preferably 250 to 350° C. A tungsten compound contained in the mixed catalyst after the calcining treatment generally has a structure different from that of the tungsten source. However, the mixed catalyst is in the category of the mixed catalyst of the present embodiment as long as the mixed catalyst contains a tungsten compound which is not a portion of the composite oxide as that after the liquid phase treatment.

(c) Mixed Catalyst

A mixed catalyst of the present embodiment is a mixed catalyst for a vapor-phase catalytic oxidation reaction or a vapor-phase catalytic ammoxidation reaction of propane or isobutane, comprising:

(a) a composite oxide represented by the following composition formula (1):

$$Mo_1V_aNb_bSb_cW_dZ_eO_n \qquad (1)$$

wherein Z represents at least one element selected from the group consisting of La, Ce, Pr, Yb, Y, Sc, Sr, and Ba; each of a, b, c, d, e, and n represents an atomic ratio of each element based on Mo atom; a is in a range of $0.01 \leq a \leq 1$; b is in a range of $0.01 \leq b \leq 1$; c is in a range of $0.01 \leq c \leq 1$; d is in a range of $0.001 \leq d \leq 1$; e is in a range of $0 \leq e \leq 1$; and n represents the number determined by a valence of a component metal; and (b) a tungsten compound at a ratio of the following formula (2):

$$0.001 < w < 0.3 \qquad (2)$$

wherein w represents an atomic ratio of tungsten in the tungsten compound as an atomic ratio based on Mo atom in the composite oxide.

The mixed catalyst of the present embodiment is a mixture of the tungsten compound and the composite oxide. The mixed catalyst contains the tungsten compound as an indispensable component, and thereby yield of a target product can be dramatically enhanced on the basis of the following principle. In the principle, a tungsten element in the tungsten compound is diffused on a surface of the composite oxide and is fixed during a vapor-phase catalytic oxidation reaction of propane or isobutane and oxygen, and a vapor-phase catalytic ammoxidation reaction of propane or isobutane, and oxygen, and ammonia.

The composition of the composite oxide of the present embodiment is represented by the following formula (1):

$$Mo_1V_aNb_bSb_cW_dZ_eO_n \qquad (1)$$

wherein Z represents at least one element selected from the group consisting of La, Ce, Pr, Yb, Y, Sc, Sr, and Ba; each of a, b, c, d, e, and n represents an atomic ratio of element based on Mo atom; a is in a range of $0.01 \leq a \leq 1$; b is in a range of $0.01 \leq b \leq 1$; c is in a range of $0.01 \leq c \leq 1$; d is in a range of $0.001 \leq d \leq 1$; e is in a range of $0 \leq e \leq 1$; and n represents a number determined by the valence of a component metal.

Preferably, a and b representing atomic ratios of V and Nb based on Mo atom are respectively 0.1 to 0.4, and 0.02 to 0.2.

c representing an atomic ratio of Sb based on Mo atom is preferably 0.01 to 0.6, and more preferably 0.1 to 0.4. a/c which was an atomic ratio of V and Sb was diligently studied. As a result, a/c is found to be preferably in the range of 0.1 to 1 from the viewpoint of enhancing yield although the detailed reason was unclear.

d representing an atomic ratio of W based on Mo atom is in the range of $0.001 \leq d \leq 1$, and preferably in the range of $0.001 \leq d \leq 0.3$. Tungsten in the composite oxide (hereinafter, tungsten which is present in the composite oxide may be referred to as "bulk tungsten") is estimated to be substituted for a molybdenum or vanadium site in the composite oxide. When the melting points of oxides are compared, for example, the melting points of molybdenum trioxide and tungsten trioxide are respectively 795° C. and 1473° C., and the melting point of the tungsten oxide is higher. Thereby, when molybdenum in the composite oxide is substituted with tungsten, the melting point of the composite oxide is estimated to be raised. Therefore, the bulk tungsten dispersed in the composite oxide is considered to have an influence on the crystal structure of the composite oxide to contribute to heat resistance and oxidation-resistant reducing properties. As a result, the composite oxide having the bulk tungsten tends to have a long catalyst life, and tends to be advantageous for industrial long-term use. On the other hand, tungsten in the tungsten compound is estimated to have an effect of enhancing yield of an unsaturated acid or an unsaturated nitrile. Further, the bulk tungsten is estimated to have an effect of suppressing the reduction of yield of a target product caused by the excessive diffusion of tungsten in the tungsten compound to the composite oxide.

e representing an atomic ratio of the component Z based on Mo atom is in the range of $0 \leq e \leq 1$, preferably in the range of $0.001 \leq e \leq 1$, more preferably in the range of $0.001 \leq e \leq 0.1$, and still more preferably in the range of $0.002 \leq e \leq 0.01$. Since the component Z produces a disadvantageous reaction in a slurry as taught in Japanese Patent Laid-Open No. 11-244702, the trace amount of the component Z is preferably contained. On the other hand, since the component Z has a high effect of enhancing yield of a target product, preferably, the component Z is uniformly dispersed in catalyst particles. The component Z represents at least one element selected from the group consisting of La, Ce, Pr, Yb, Y, Sc, Sr, and Ba, preferably one or more elements selected from the group consisting of La, Ce, Pr, and Yb, and particularly preferably Ce, since Ce tends to provide the highest yield of the target product.

The composite oxide is preferably carried by a carrier containing silica as a main component. When the composite oxide is carried by the carrier containing silica as a main component, the composite oxide has high mechanical strength, and thereby the composite oxide is appropriate for a vapor-phase catalytic oxidation reaction or a vapor-phase catalytic ammoxidation reaction using a fluidized bed reactor. A content of silica in the carrier containing silica as a main component is, in terms of $SiO_2$ preferably 20 to 70% by mass, and more preferably 30 to 60% by mass on the basis of an entire mass of a carried oxide containing an oxide of an element composing the composite oxide and the carrier.

The content of silica in the composite oxide is preferably 20% by mass or more from the viewpoint of strength and powdering prevention. When the content of silica is less than 20% by mass, it is difficult to stably operate the composite oxide when industrially using the composite oxide, and it is necessary to fill the lost composite oxide. Thereby, the content of silica of less than 20% by mass is economically disadvantageous. To the contrary, when the content of silica is more than 70% by mass, insufficient activity is obtained, thereby increasing the amount of a required catalyst. Particularly, when the content of silica is more than 70% by mass in the case of a fluidized bed, the specific gravity of silica support particles is excessively light, and thereby a good flow state is hardly obtained.

The mixed catalyst of the present embodiment contains the composite oxide represented by the above-mentioned composition formula (1) and the tungsten compound at the ratio of the following formula (2).

$$0.001 < w < 0.3 \tag{2}$$

In the formula (2), w represents an atomic ratio of tungsten in the tungsten compound as an atomic ratio based on Mo atom in the composite oxide.

w which represents an atomic ratio of tungsten in the tungsten compound based on Mo atom of the composite oxide is in the range of $0.001 < w < 0.3$, preferably in the range of $0.01 < w < 0.2$, and more preferably in the range of $0.015 < w < 0.18$. When w is 0.001 or less, an amount of tungsten is too small, and thereby enhancement of the yield of a target product cannot be confirmed. When w is 0.3 or more, the amount of tungsten is excessive, and thereby the surface of the catalyst is not reformed to a preferred form. Again, the effect of enhancing the yield of a target product cannot be obtained.

The composition of the mixed catalyst and the composition of the composite oxide are measured by fluorescent X-ray analysis, and the amount of w is determined from the following formula:

$w$=(W composition ratio in mixed catalyst)−(W composition ratio in composite oxide)

A compound having a low melting point may be crystallized in a protruded state on the surface of the composite oxide particles after main calcination. Even when the crystal is removed from the surface of the catalyst by contact between catalysts, or the like, w is hardly influenced. Therefore, the amount of w may be determined by composition analysis at any stage before and after removing the crystal of the oxide.

The composite oxide and the tungsten compound are preferably brought into contact with each other in the mixed catalyst. Particles of micrometer or millimeter order may be brought into contact with one another, or the tungsten compound and the composite oxide dispersed in a nano order in fine pores in the composite oxide particles may be brought into contact with one another. For example, the former is obtained by physically mixing the composite oxide particles and the tungsten source, and the latter is obtained by the liquid phase treatment using the composite oxide particles and a liquid tungsten source.

Even when structural analysis by X-ray diffraction or the like is carried out on the mixed catalyst of the present embodiment, it is difficult to confirm change in the structure of the mixed catalyst before and after the mixing treatment. When the target product is produced using the mixed catalyst, no difference is generally observed at the stage immediately after reaction initiation as compared with the performance of the composite oxide which does not contain the tungsten compound. For example, when the production reaction of the unsaturated nitrile is carried out at 445° C., no difference between the yields of the target products in the mixed catalyst and the composite oxide is substantially observed after 5 hours from the reaction initiation. On the other hand, the difference between the yields of both the reactions appears with the lapse of the reaction time. For example, the enhancement of the yield of 1% or more is observed as compared with the first stage in the reaction using the mixed catalyst after 240 Hr. However, in the case of the composite oxide, the initial yield is hardly changed.

The reason why the yield of the target product is improved during the production reaction of the unsaturated acid or the unsaturated nitrile using the mixed catalyst of the present embodiment will be described below. The present inventors estimate that tungsten in the tungsten compound is diffused on the surface of the composite oxide in a solid phase reaction, and the exchange reaction of tungsten and a metal element such as Mo occurs, thereby reforming the surface of the catalyst to a preferred form. The preferred form of the surface of the catalyst and the mechanism of performance improvement are unclear. Tungsten is estimated to be disposed at a specific site near the surface the composite oxide to suppress the successive decomposition of the target product or an intermediate product. As described above, the structure and the dispersion state of the tungsten compound is considered to be different depending on the preparing method or the like of the mixed catalyst. However, in accordance with the consideration of the present inventors, the difference of the performance depending on the structure or the dispersion state of the tungsten compound was hardly observed in the mixed catalyst before the solid phase reaction. It is important that the mixed catalyst contains only an appropriate amount of the tungsten compound independently of the composite oxide. The solid phase reaction is estimated to occur during the production reaction over a long period of time as long as the content of the tungsten compound is in an appropriate range regardless of the state of the tungsten compound. When a reaction is performed for a long period of time using a general mixed catalyst, Mo in the catalyst is reduced with time. In this case, a method for introducing a Mo compound into a reactor and suppressing activity reduction caused by the reduction of the Mo composition (makeup technique) has been known as a known technique. The makeup technique for the Mo compound can be used together in the production reaction of the unsaturated acid or the unsaturated nitrile using the mixed catalyst of the present embodiment.

[2] Unsaturated Acid or Unsaturated Nitrile

In the presence of the mixed catalyst of the present embodiment, propane or isobutane is subjected to a vapor-phase catalytic oxidation or a vapor-phase catalytic ammoxidation reaction, thereby producing a corresponding unsaturated acid or unsaturated nitrile.

That is, a method for producing an unsaturated acid or an unsaturated nitrile of the present embodiment includes the step of bringing propane or isobutane and oxygen into contact with the above-mentioned mixed catalyst, or bringing propane or isobutane, and oxygen and ammonia into contact with the mixed catalyst.

When the mixed catalyst of the present embodiment is used, yield of a target product approaches a maximum value with the lapse of the production reaction of the unsaturated acid or the unsaturated nitrile. Although the detailed reason is unclear, it is estimated that the solid phase reaction of tungsten in the tungsten compound is appropriately progressed in the vapor-phase catalytic oxidation reaction using propane or isobutane and air, or in the vapor-phase catalytic ammoxidation reaction using propane or isobutane, and air and ammonia, and thereby the mixed catalyst is activated. This is because the yield of the target product is not improved at all in air atmosphere calcination and nitrogen atmosphere calcination at 300 to 550° C. in the basic consideration of the present embodiment. A preferable condition for the activation is not particularly limited. However, propane or isobutane and oxygen are preferably heated at 350 to 550° C., and more preferably at 400 to 500° C. with the propane or isobutane and oxygen brought into contact with the mixed catalyst. Alternatively, propane or isobutane, and oxygen and ammonia are preferably heated at 350 to 550° C., and more preferably at 400 to 500° C. with the propane or isobutane, and oxygen and ammonia brought into contact with the mixed catalyst. On the other hand, an activating treatment time is preferably 1 to 1500 hours, more preferably 5 to 750 hours, and still more preferably 50 to 500 hours.

Supply raw materials of propane or isobutane and ammonia are not necessarily highly pure, and those of industrial-grade gas can be used.

Air, air enriched with oxygen or pure oxygen can be used as a supply oxygen source. Further, as a dilution gas, helium, argon, carbon dioxide, steam, and nitrogen or the like may be supplied.

A vapor-phase catalytic oxidation reaction of propane or isobutane can be performed under the following conditions.

A molar ratio of oxygen to be supplied for the reaction to propane or isobutane is 0.1 to 6, and preferably 0.5 to 4.

A reaction temperature is 300 to 500° C., and preferably 350 to 450° C.

A reaction pressure is $5 \times 10^4$ to $5 \times 10^5$ Pa, and preferably $1 \times 10^5$ to $3 \times 10^5$ Pa.

A contact time is 0.1 to 10 (sec·g/cc), and preferably 0.5 to 5 (sec·g/cc). In the present embodiment, the contact time is determined by the following formula.

$$\text{Contact time (sec·g/cc)} = (W/F) \times 273/(273+T)$$

Here, W, F and T are defined as follows:

W=Amount (g) of catalyst packed

F=Flow rate (Ncc/sec) of raw material mixed gas under normal conditions (0° C., $1.013 \times 10^5$ Pa)

T=Reaction temperature (° C.)

A vapor-phase catalytic ammoxidation reaction of propane or isobutane can be performed under the following conditions:

A molar ratio of oxygen to be supplied for the reaction to propane or isobutane is 0.1 to 6, and preferably 0.5 to 4.

A molar ratio of ammonia to be supplied for the reaction to propane or isobutane is 0.3 to 1.5, and preferably 0.7 to 1.2.

A reaction temperature is 350 to 500° C., and preferably 380 to 470° C.

A reaction pressure is $5 \times 10^4$ to $5 \times 10^5$ Pa, and preferably $1 \times 10^5$ to $3 \times 10^5$ Pa.

A contact time is 0.1 to 10 (sec·g/cc), and preferably 0.5 to 5 (sec·g/cc).

As a reaction method, any one of conventional methods such as a fixed bed method, a fluidized bed method and a moving bed method can be adopted. However, a fluidized bed reactor providing easiness of removal of reaction heat is preferable. The vapor-phase catalytic oxidation or the ammoxidation reaction may either be a single current system or a recycle system.

EXAMPLES

Hereinafter, the present embodiment will be further described in detail with reference to examples and comparative examples. However, the range of the present embodiment is not limited to the examples.

In the examples and the comparative examples, a ratio of propane conversion and yield of acrylonitrile respectively follow the following definitions.

Ratio of propane conversion (%)=(Number of moles of reacted propane)/(Number of moles of supplied propane)×100

Yield of Acrylonitrile (AN) (%)=(Number of moles of produced acrylonitrile)/(Number of moles of supplied propane)×100

(Preparation of Niobium Mixed-Solution)

A niobium mixed-solution was prepared by a method as described below.

To 10 kg of water, 0.765 kg of niobic acid containing 80.0% by mass of niobium in terms of $Nb_2O_5$ and 2.633 kg of oxalic acid dihydrate [$H_2C_2O_4.2H_2O$] were added. A molar ratio of oxalic acid/niobium as feedstocks was 5.0 and a concentration of feedstock niobium was 0.50 (mol-Nb/kg-solution). The resultant solution was heated for two hours at 95° C. with stirring, thereby obtaining a mixed-solution in which niobium was dissolved. This mixed-solution was left standstill, cooled with ice, subjected to a suction filtration for removing a solid content, thereby obtaining a uniform niobium mixed-solution. The molar ratio of the oxalic acid/niobium of this niobium mixed-solution was 2.71 by the analysis described below.

10 g of this niobium mixed-solution was precisely weighed and put in a crucible, dried for a night at 95° C., and subjected to a heat treatment for one hour at 600° C., thereby obtaining 0.771 g of $Nb_2O_5$. From this result, the niobium concentration was 0.580 (mol-Nb/kg-solution).

3 g of this niobium mixed-solution was precisely weighed and put in a glass beaker having a capacity of 300 ml, added with 200 ml of hot water having a temperature of about 80° C. and, then, added with 10 ml of a 1:1 sulfuric acid. The resultant mixed-solution was titrated by using a ¼ N $KMnO_4$ solution with stirring while being kept at a temperature of 70° C. on a hot stirrer. A point at which a faint light pink color by $KMnO_4$ lasted for about 30 seconds or more was defined as an end-point. A concentration of oxalic acid was determined on the basis of the resultant titer in accordance with the following formula and, as a result, it was 1.570 (mol-oxalic acid/kg).

$2KMnO_4+3H_2SO_4+5H_2C_2O_4 \rightarrow K_2SO_4+2MnSO_4+10CO_2+8H_2O$

The obtained niobium mixed-solution was used as a niobium mixed-solution ($B_0$) for use in preparation of a catalyst to be described below.

Example 1

Preparation of Composite Oxide

A composite oxide having a feedstock composition formula represented by $Mo_1V_{0.21}Nb_{0.10}Sb_{0.24}W_{0.03}Ce_{0.005}O_n$/47.0% by weight-$SiO_2$ was produced as follows.

To 1.902 kg of water, 424.3 g of ammonium heptamolybdate [$(NH_4)_6Mo_7O_{24}.4H_2O$], 59.0 g of ammonium metavanadate [$NH_4VO_3$], 5.22 g of cerium nitrate hexahydrate, and 87.6 g of diantimony trioxide [$Sb_2O_3$] were added and heated for 1 hour at 95° C. with stirring, thereby obtaining an aqueous raw-material solution (I).

To 414.3 g of a niobium mixed-solution ($B_0$), 54.5 g of a hydrogen peroxide solution containing 30% by weight of $H_2O_2$ was added and mixed for 10 minutes at room temperature with stirring, thereby preparing an aqueous raw-material solution (II).

After the obtained aqueous raw-material solution (I) was cooled to 70° C., 760.3 g of silica sol containing 34.0% by weight of $SiO_2$ was added thereto and, further, 102.2 g of a hydrogen peroxide solution containing 30% by weight of $H_2O_2$ was added thereto and then, the resultant mixture was continuously stirred for 30 minutes at 55° C. Next, the aqueous raw-material solution (II), 33.4 g of an aqueous solution of ammonium metatungstate containing 50% by weight of $WO_3$, and a dispersion liquid in which 211.5 g of silica powder was dispersed in 2.750 kg of water were sequentially added thereto, thereby obtaining an aqueous mixed-solution (III). The aqueous mixed-solution (III) was aged at 50° C. for 2 hours and 30 minutes after the aqueous raw-material solution (II) was added, thereby obtaining a slurry.

The obtained slurry was supplied to a centrifugal spray dryer and dried, thereby obtaining a microspherical dry powder. Temperatures at an inlet and an outlet of the dryer were respectively 210° C. and 120° C.

800 g of the obtained dry powder was packed in a calcining tube having a diameter of 3 inches and made of SUS, and then, calcined for 2 hours at 680° C. in a flow of a nitrogen gas at a rate of 8.0 NL/min while the tube was rotated, thereby obtain a composite oxide.

(Preparation of Mixed Catalyst)

100 g of the obtained composite oxide was added to an aqueous solution (W concentration: 0.7 mol/kg) with stirring, and mixed. The aqueous solution was obtained by diluting 46.2 g of an aqueous solution of ammonium metatungstate with 453.8 g of water. The obtained mixed-solution was moved into an aspirator container, and was then subjected to a reduced-pressure treatment at 100 kPa for 10 minutes. The mixed-solution in the aspirator was then filtered, and the resulting solid was subjected to a drying treatment at 50° C. for 12 hours in a drier, thereby obtaining a mixture of the composite oxide and a tungsten compound. The compositions of the obtained composite oxide and mixed catalyst were analyzed. A fluorescent X-ray analyzer (RIX1000, manufactured by Rigaku Corporation) was used for composition analysis.

The composition of the composite oxide was $Mo_1V_{0.21}Nb_{0.10}Sb_{0.24}W_{0.03}Ce_{0.005}O_n$, and the composition of the mixed catalyst was $Mo_1V_{0.21}Nb_{0.10}Sb_{0.24}W_{0.10}Ce_{0.005}O_n$. From the difference between the W composition ratios of the composite oxide and the mixed catalyst, it was confirmed that w was 0.07.

(Ammoxidation Reaction of Propane)

35 g of the obtained mixed catalyst was packed in a Vycor glass fluidized-bed reaction tube having an inner diameter of 25 mm. A mixed gas having a molar ratio of propane:ammonia:oxygen:helium of 1:1:3:18 was supplied into the reaction tube at a rate of contact period of time of 3.4 (sec·g/cc) at a reaction temperature of 445° C. under a reaction pressure of 0.05 Mpa. After the lapse of 5 hours after the supply of the mixed gas was started, the propane conversion was 88.3%, and the AN yield was 52.4%.

The reaction was then continued under the same conditions. After the lapse of 240 hours after the supply of the mixed gas was started, the propane conversion was 88.8%, and the AN yield was 54.4%.

Example 2

Production of Mixed Catalyst

A mixed catalyst was produced using the composite oxide obtained in the example 1. The mixed catalyst was produced in the same manner as in the example 1 except that a W concentration of a diluted aqueous solution of ammonium tungstate was changed to 1.5 mol/kg.

As a result of measuring the composition of the obtained mixed catalyst in the same manner as in the example 1, it was confirmed that the composition was $Mo_1V_{0.21}Nb_{0.10}Sb_{0.24}W_{0.18}Ce_{0.005}O_n$, and w was 0.15.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.2%, and the AN yield was 52.3%.

The reaction was then continued under the same conditions. After the lapse of 240 hours after the supply of the mixed gas was started, the propane conversion was 88.6%, and the AN yield was 53.8%.

Comparative Example 1

Preparation of Composite Oxide

A composite oxide having a feedstock composition formula represented by $Mo_1V_{0.21}Nb_{0.10}Sb_{0.24}Ce_{0.005}O_n/47.0\%$ by weight-$SiO_2$ was produced as follows.

To 1.964 kg of water, 441.1 g of ammonium heptamolybdate [$(NH_4)_6Mo_7O_{24}.4H_2O$], 61.4 g of ammonium metavanadate [$NH_4VO_3$], 5.42 g of cerium nitrate hexahydrate, and 87.4 g of diantimony trioxide [$Sb_2O_3$] were added and heated for 1 hour at 95° C. with stirring, thereby obtaining an aqueous raw-material solution (I).

To 430.8 g of a niobium mixed-solution ($B_0$), 56.7 g of a hydrogen peroxide solution containing 30% by weight of $H_2O_2$ was added and mixed with stirring for 10 minutes at room temperature, thereby preparing an aqueous raw-material solution (II).

After the obtained aqueous raw-material solution (I) was cooled to 70° C., 760.3 g of silica sol containing 34.0% by weight of $SiO_2$ was added thereto and, further, 102.2 g of a hydrogen peroxide solution containing 30% by weight of $H_2O_2$ was added thereto and then, the resultant mixture was continuously stirred for 30 minutes at 55° C. Next, the aqueous raw-material solution (II), and a dispersion liquid in which 211.5 g of silica powder was dispersed in 2.750 kg of water were sequentially added thereto, thereby obtaining an aqueous mixed-solution (III). The aqueous mixed-solution (III) was aged at 50° C. for 2 hours and 30 minutes after the aqueous raw-material solution (II) was added, thereby obtaining a slurry.

The obtained slurry was supplied to a centrifugal spray dryer and dried, thereby obtaining a microspherical dry powder. Temperatures at an inlet and an outlet of the dryer were respectively 210° C. and 120° C.

800 g of the obtained dry powder was packed in a calcining tube having a diameter of 3 inches and made of SUS, and then, calcined for 2 hours at 680° C. in a flow of a nitrogen gas at a rate of 8.0 NL/min while the tube was rotated, thereby obtain a composite oxide.

(Production of Mixed Catalyst)

100 g of the obtained composite oxide was added to an aqueous solution (W concentration: 1.0 mol/kg) with stirring, and mixed. The aqueous solution was obtained by diluting 231.0 g of an aqueous solution of ammonium metatungstate containing 50.0% by weight of $WO_3$ with 453.8 g of water. The obtained mixed-solution was moved into an aspirator container, and was then subjected to a reduced-pressure treatment at 100 kPa for 10 minutes. The mixed-solution in the aspirator was then filtered, and the resulting solid was subjected to a drying treatment at 50° C. for 12 hours in a drier, thereby obtaining a mixture of the composite oxide and a tungsten compound. The compositions of the obtained composite oxide and mixed catalyst were analyzed. A fluorescent X-ray analyzer (RIX1000, manufactured by Rigaku Corporation) was used for composition analysis.

The composition of the obtained composite oxide was $Mo_1V_{0.21}Nb_{0.10}Sb_{0.24}Ce_{0.005}O_n$, and the composition of the mixed catalyst was $Mo_1V_{0.21}Nb_{0.10}Sb_{0.24}W_{0.10}Ce_{0.005}O_n$. From the difference between the W composition ratios of the composite oxide and the mixed catalyst, it was confirmed that w was 0.10.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.3%, and the AN yield was 52.2%.

The reaction was then continued under the same conditions. After the lapse of 240 hours after the supply of the mixed gas was started, the propane conversion was 86.3%, and the AN yield was 51.8%.

Comparative Example 2

Production of Mixed Catalyst

A mixed catalyst was produced in the same manner as in the comparative example 1 except that a W concentration of a diluted aqueous solution of ammonium tungstate was changed to 1.5 mol/kg.

As a result of measuring the composition of the obtained mixed catalyst in the same manner as in the comparative example 1, it was confirmed that the composition was $Mo_1V_{0.21}Nb_{0.10}Sb_{0.24}W_{0.15}Ce_{0.005}O_n$, and w was 0.15.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 86.9%, and the AN yield was 51.8%.

The reaction was then continued under the same conditions. After the lapse of 240 hours after the supply of the mixed gas was started, the propane conversion was 85.2%, and the AN yield was 50.3%.

Example 3

Production of Mixed Catalyst

An aqueous solution in which 500 g of an aqueous solution of ammonium metatungstate was diluted with 500 g of water was prepared. The obtained aqueous solution was supplied to a centrifugal spray dryer and dried, thereby obtaining a microspherical dry powder. Temperatures at an inlet and an outlet of the dryer were respectively 210° C. and 120° C. 100 g of the obtained tungsten-containing spray-dried product was calcined at 500° C. under an air atmosphere for 2 hours, thereby obtaining a powdered tungsten compound. X-ray diffraction measurement was used to confirm that the tungsten compound was tungsten trioxide.

100 g of the composite oxide obtained in the example 1 and 3.37 g of the obtained tungsten compound were mixed in powder, thereby obtaining a mixed catalyst. The composition of the obtained mixed catalyst was analyzed. A fluorescent X-ray analyzer (RIX1000, manufactured by Rigaku Corporation) was used for composition analysis.

It was confirmed that the composition of the obtained mixed catalyst was $Mo_1V_{0.21}Nb_{0.10}Sb_{0.24}W_{0.09}Ce_{0.005}O_n$, and w was 0.06.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.7%, and the AN yield was 52.6%.

The reaction was then continued under the same conditions. After the lapse of 240 hours after the supply of the mixed gas was started, the propane conversion was 89.2%, and the AN yield was 54.0%.

Example 4

Production of Mixed Catalyst

A mixed catalyst was obtained in the same manner as in the example 3 except that a mass of a tungsten compound to be mixed was changed to 10.1 g. The composition of the obtained mixed catalyst was analyzed in the same manner as in the example 1. A fluorescent X-ray analyzer (RIX1000, manufactured by Rigaku Corporation) was used for composition analysis.

It was confirmed that the composition of the obtained mixed catalyst was $Mo_1V_{0.21}Nb_{0.10}Sb_{0.24}W_{0.18}Ce_{0.005}O_n$, and w was 0.15.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.6%, and the AN yield was 52.5%.

The reaction was then continued under the same conditions. After the lapse of 240 hours after the supply of the mixed gas was started, the propane conversion was 89.0%, and the AN yield was 53.6%.

Comparative Example 3

Production of Mixed Catalyst

A mixed catalyst was produced in the same manner as in the example 3 except that the composite oxide obtained in the comparative example 1 was used and a mass of a tungsten compound to be mixed was changed to 6.74 g.

As a result of measuring the composition of the obtained mixed catalyst in the same manner as in the example 1, it was confirmed that the composition was $Mo_1V_{0.21}Nb_{0.10}Sb_{0.24}W_{0.10}Ce_{0.005}O_n$, and w was 0.10.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.6%, and the AN yield was 52.5%.

The reaction was then continued under the same conditions. After the lapse of 240 hours after the supply of the mixed gas was started, the propane conversion was 87.6%, and the AN yield was 52.1%.

Comparative Example 4

Production of Mixed Catalyst

A mixed catalyst was prepared in the same manner as in the example 3 except that the composite oxide obtained in the comparative example 1 was used and a mass of a tungsten compound to be mixed was changed to 10.1 g.

As a result of measuring the composition of the obtained mixed catalyst in the same manner as in the example 1, it was confirmed that the composition was $Mo_1V_{0.21}Nb_{0.10}Sb_{0.24}W_{0.15}Ce_{0.005}O_n$, and w was 0.15.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.5%, and the AN yield was 52.4%.

The reaction was then continued under the same conditions. After the lapse of 240 hours after the supply of the mixed gas was started, the propane conversion was 86.3%, and the AN yield was 50.9%.

Comparative Example 5

Ammoxidation Reaction of Propane

An ammoxidation reaction of propane was performed in the same manner as in the example 1 using the composite oxide obtained in the example 1 as it is, without producing a mixed catalyst. After the lapse of 5 hours after the supply of a mixed gas was started, the propane conversion was 88.4%, and the AN yield was 52.2%.

The reaction was then continued under the same conditions. After the lapse of 240 hours after the supply of the mixed gas was started, the propane conversion was 88.3%, and the AN yield was 52.1%.

Example 5

Preparation of Composite Oxide

A composite oxide represented by a feedstock composition formula: $Mo_1V_{0.21}Nb_{0.10}Sb_{0.24}W_{0.12}Ce_{0.005}O_n$/47.0% by weight-$SiO_2$ was produced by the same method as that of the example 1 except that an added amount of an aqueous solution of ammonium metatungstate was changed to 133.6 g.

(Production of Mixed Catalyst)

A mixed catalyst was produced in the same manner as in the example 1 using the obtained composite oxide. As a result of measuring the compositions of the composite oxide and the mixed catalyst by the same method as that of the example 1, the composition of the composite oxide was $Mo_1V_{0.21}Nb_{0.10}Sb_{0.24}W_{0.12}Ce_{0.005}O_n$, and the composition of the mixed catalyst was $Mo_1V_{0.21}Nb_{0.10}Sb_{0.24}W_{0.19}Ce_{0.005}O_n$. From the W composition ratios of the composite oxide and the mixed catalyst, it was confirmed that w was 0.07.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.6%, and the AN yield was 52.1%.

The reaction was then continued under the same conditions. After the lapse of 240 hours after the supply of the mixed gas was started, the propane conversion was 87.7%, and the AN yield was 54.1%.

Example 6

A mixed catalyst was produced in the same manner as in the example 2 using the composite oxide obtained in the example 5.

As a result of measuring the composition of the obtained mixed catalyst in the same manner as in the example 1, it was confirmed that the composition was $Mo_1V_{0.21}Nb_{0.10}Sb_{0.24}W_{0.27}Ce_{0.005}O_n$, and w was 0.15.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.5%, and the AN yield was 52.0%.

The reaction was then continued under the same conditions. After the lapse of 240 hours after the supply of the mixed gas was started, the propane conversion was 87.6%, and the AN yield was 53.6%.

Example 7

Production of Mixed Catalyst

A mixed catalyst was produced using the composite oxide obtained in the example 1. The mixed catalyst was produced in the same manner as in the example 1 except that a W concentration of a diluted aqueous solution of ammonium tungstate was changed to 0.2 mol/kg.

As a result of measuring the composition of the obtained mixed catalyst in the same manner as in the example 1, it was confirmed that the composition was $Mo_1V_{0.21}Nb_{0.10}Sb_{0.24}W_{0.05}Ce_{0.005}O_n$, and w was 0.02.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.3%, and the AN yield was 52.3%.

The reaction was then continued under the same conditions. After the lapse of 240 hours after the supply of the mixed gas was started, the propane conversion was 88.9%, and the AN yield was 55.1%.

Example 8

Production of Mixed Catalyst

A mixed catalyst was produced using the composite oxide obtained in the example 1. The mixed catalyst was produced in the same manner as in the example 1 except that a W concentration of a diluted aqueous solution of ammonium tungstate was changed to 0.3 mol/kg.

As a result of measuring the composition of the obtained mixed catalyst in the same manner as in the example 1, it was confirmed that the composition was $Mo_1V_{0.21}Nb_{0.10}Sb_{0.24}W_{0.06}Ce_{0.005}O_n$, and w was 0.03.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.4%, and the AN yield was 52.4%.

The reaction was then continued under the same conditions. After the lapse of 240 hours after the supply of the mixed gas was started, the propane conversion was 89.2%, and the AN yield was 55.2%.

Comparative Example 6

Production of Mixed Catalyst

A mixed catalyst was produced using the composite oxide obtained in the comparative example 1. The mixed catalyst was produced in the same manner as in the comparative example 1 except that a W concentration of a diluted aqueous solution of ammonium tungstate was changed to 0.05 mol/kg.

As a result of measuring the composition of the obtained mixed catalyst in the same manner as in the comparative example 1, it was confirmed that the composition was $Mo_1V_{0.21}Nb_{0.10}Sb_{0.24}W_{0.005}Ce_{0.005}O_n$, and w was 0.005.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 88.3%, and the AN yield was 52.1%.

The reaction was then continued under the same conditions. After the lapse of 240 hours after the supply of the mixed gas was started, the propane conversion was 88.2%, and the AN yield was 52.0%.

Comparative Example 7

Production of Mixed Catalyst

A mixed catalyst was produced using the composite oxide obtained in the example 1. The mixed catalyst was obtained in the same manner as in the example 3 except that a mass of a tungsten compound to be mixed was changed to 44.9 g.

As a result of measuring the composition of the obtained mixed catalyst in the same manner as in the example 1, it was confirmed that the composition was $Mo_1V_{0.21}Nb_{0.10}Sb_{0.24}W_{0.24}Ce_{0.005}O_n$, and w was 0.40.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 86.2%, and the AN yield was 51.9%.

The reaction was then continued under the same conditions. After the lapse of 240 hours after the supply of the mixed gas was started, the propane conversion was 83.5%, and the AN yield was 49.3%.

Example 9

Preparation of Composite Oxide

A composite oxide represented by a feedstock composition formula: $Mo_1V_{0.21}Nb_{0.10}Sb_{0.24}W_{0.03}O_n/47.0\%$ by weight-$SiO_2$ was produced by the same method as that of the example 1 except that 5.22 g of cerium nitrate hexahydrate was not added.

(Production of Mixed Catalyst)

A mixed catalyst was produced in the same manner as in the example 7 using the obtained composite oxide. As a result of measuring the compositions of the composite oxide and the mixed catalyst by the same method as that of the example 1, the composition of the composite oxide was $Mo_1V_{0.21}Nb_{0.10}Sb_{0.24}W_{0.03}O_n$, and the composition of the mixed catalyst was $Mo_1V_{0.21}Nb_{0.10}Sb_{0.24}W_{0.05}O_n$. From the W composition ratios of the composite oxide and the mixed catalyst, it was confirmed that w was 0.02.

(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 85.8%, and the AN yield was 51.0%.

Example 10

Preparation of Composite Oxide

A composite oxide represented by a feedstock composition formula: $Mo_1V_{0.21}Nb_{0.10}Sb_{0.24}W_{0.03}La_{0.005}O_n/47.0\%$ by weight-$SiO_2$ was produced by the same method as that of the example 1 except that 5.21 g of lanthanum nitrate hexahydrate was added in place of 5.22 g of cerium nitrate hexahydrate.
(Production of Mixed Catalyst)

A mixed catalyst was produced in the same manner as in the example 7 using the obtained composite oxide. As a result of measuring the compositions of the composite oxide and the mixed catalyst by the same method as that of the example 1, the composition of the composite oxide was $Mo_1V_{0.21}Nb_{0.10}Sb_{0.24}W_{0.03}La_{0.005}O_n$, and the composition of the mixed catalyst was $Mo_1V_{0.21}Nb_{0.10}Sb_{0.24}W_{0.05}La_{0.005}O_n$. From the W composition ratios of the composite oxide and the mixed catalyst, it was confirmed that w was 0.02.
(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.6%, and the AN yield was 51.8%.

The reaction was then continued under the same conditions. After the lapse of 240 hours after the supply of the mixed gas was started, the propane conversion was 87.9%, and the AN yield was 53.6%.

Example 11

Preparation of Composite Oxide

A composite oxide represented by a feedstock composition formula: $Mo_1V_{0.21}Nb_{0.10}Sb_{0.24}W_{0.03}Pr_{0.005}O_n/47.0\%$ by weight-$SiO_2$ was produced by the same method as that of the example 1 except that 5.23 g of praseodymium nitrate hexahydrate was added in place of 5.22 g of cerium nitrate hexahydrate.
(Production of Mixed Catalyst)

A mixed catalyst was produced in the same manner as in the example 7 using the obtained composite oxide. As a result of measuring the compositions of the composite oxide and the mixed catalyst by the same method as that of the example 1, the composition of the composite oxide was $Mo_1V_{0.21}Nb_{0.10}Sb_{0.24}W_{0.03}Pr_{0.005}O_n$, and the composition of the mixed catalyst was $Mo_1V_{0.21}Nb_{0.10}Sb_{0.24}W_{0.05}Pr_{0.005}O_n$. From the W composition ratios of the composite oxide and the mixed catalyst, it was confirmed that w was 0.02.
(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.9%, and the AN yield was 52.4%.

The reaction was then continued under the same conditions. After the lapse of 240 hours after the supply of the mixed gas was started, the propane conversion was 88.5%, and the AN yield was 54.4%.

Example 12

Preparation of Composite Oxide

A composite oxide represented by a feedstock composition formula: $Mo_1V_{0.21}Nb_{0.10}Sb_{0.24}W_{0.03}Yb_{0.005}O_n/47.0\%$ by weight-$SiO_2$ was produced by the same method as that of the example 1 except that 4.97 g of ytterbium nitratetrihydrate was added in place of 5.22 g of cerium nitrate hexahydrate.
(Production of Mixed Catalyst)

A mixed catalyst was produced in the same manner as in the example 7 using the obtained composite oxide. As a result of measuring the compositions of the composite oxide and the mixed catalyst by the same method as that of the example 1, the composition of the composite oxide was $Mo_1V_{0.21}Nb_{0.10}Sb_{0.24}W_{0.03}Yb_{0.005}O_n$, and the composition of the mixed catalyst was $Mo_1V_{0.21}Nb_{0.10}Sb_{0.24}W_{0.05}Yb_{0.005}O_n$. From the W composition ratios of the composite oxide and the mixed catalyst, it was confirmed that w was 0.02.
(Ammoxidation Reaction of Propane)

An ammoxidation reaction of propane was performed in the same manner as in the example 1 using the obtained mixed catalyst. After the lapse of 5 hours after the supply of a mixed gas was started, the propane conversion was 87.7%, and the AN yield was 52.4%.

The reaction was then continued under the same conditions. After the lapse of 240 hours after the supply of the mixed gas was started, the propane conversion was 88.2%, and the AN yield was 54.3%.

The present application is based on Japanese Patent Applications (Nos. 2010-111422 and 2010-111444) filed to the Japanese Patent Office on May 13, 2010, the contents of which are incorporated herein by reference.

The mixed catalyst of the present invention can be usefully used for an industrial producing process subjecting propane or isobutane to the vapor-phase catalytic oxidation reaction or the vapor-phase catalytic ammoxidation reaction to produce the corresponding unsaturated acid or unsaturated nitrile.

What is claimed is:
1. A mixed catalyst for a vapor-phase catalytic oxidation reaction or a vapor-phase catalytic ammoxidation reaction of propane or isobutane,
the mixed catalyst comprising:
(a) a composite oxide represented by the following composition formula (1):

$$Mo_1V_aNb_bSb_cW_dZ_eO_n \quad (1)$$

wherein Z represents at least one element selected from the group consisting of La, Ce, Pr, Yb, Y, Sc, Sr, and Ba; each of a, b, c, d, e, and n represents an atomic ratio of each element based on Mo atom; a is in a range of $0.01 \le a \le 1$; b is in a range of $0.01 \le b \le 1$; c is in a range of $0.01 \le c \le 1$; d is in a range of $0.001 \le d \le 1$; e is in a range of $0 \le e \le 1$; and n represents a number determined by a valence of a component metal; and
(b) a tungsten compound at a ratio of the following formula (2):

$$0.001 < w < 0.3 \quad (2)$$

wherein w represents an atomic ratio of tungsten in the tungsten compound as an atomic ratio based on Mo atom in the composite oxide.

2. The mixed catalyst according to claim 1, wherein the tungsten compound contains tungsten oxide.

3. The mixed catalyst according to claim 1 or 2, wherein the mixed catalyst is used for a fluidized bed reaction.

4. A method for producing an unsaturated acid or an unsaturated nitrile, comprising a step of contacting propane or isobutane and oxygen with the mixed catalyst of claim 1 or 2, or contacting propane or isobutane, and oxygen and ammonia with the mixed catalyst of claim 1 or 2.

5. The method according to claim 4, wherein a temperature for the step of contacting is set to 400° C. or more.

* * * * *